United States Patent [19]

Chavdarian et al.

[11] Patent Number: 4,752,604

[45] Date of Patent: Jun. 21, 1988

[54] S,S-DI-(TERTIARY ALKYL) THIOPHOSPHONATE INSECTICIDES

[75] Inventors: Charles G. Chavdarian, Martinez; Lydia L. Chang, Orinda; Bruce C. Onisko, Albany; Jonathan P. Earhart, Orinda, all of Calif.

[73] Assignee: Stauffer Chemical Company, Westport, Conn.

[21] Appl. No.: 879,044

[22] Filed: Jul. 3, 1986

Related U.S. Application Data

[63] Continuation-in-part of Ser. No. 759,775, Jul. 29, 1985, abandoned.

[51] Int. Cl.$^4$ .......................... A01N 57/04; C07F 9/40
[52] U.S. Cl. ..................................... 514/141; 558/214
[58] Field of Search .......................... 514/141; 558/214

[56] References Cited

U.S. PATENT DOCUMENTS 3,094,405 6/1963 Toy et al. ........................... 558/203

FOREIGN PATENT DOCUMENTS 210608 2/1987 European Pat. Off. .

*Primary Examiner*—Anton H. Sutto
*Attorney, Agent, or Firm*—Joel G. Ackerman

[57] ABSTRACT

Compounds having the formula

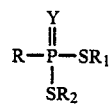

in which R is methyl or ethyl, Y is sulfur or oxygen, and $R_1$ and $R_2$ are the same or different tertiary alkyl groups each having from 4 to 6 carbon atoms, are insecticides and nematicides, especially for control of soil insects and nematodes.

Symmetrical compounds ($R_1=R_2$) may be prepared by reaction of an alkali metal mercaptide with an alkyl (thio) phosphonic dihalide. The alkali metal mercaptide may be prepared by reaction of a tertiary alkyl mercaptan with an alkali metal or alkali metal hydride.

28 Claims, No Drawings

S,S-DI-(TERTIARY ALKYL) THIOPHOSPHONATE INSECTICIDES

This application is a continuation-in-part of Ser. No. 759,775, filed July 29, 1985, now abandoned.

BACKGROUND AND PRIOR ART

This invention relates to a novel class of trialkyl thiophosphonates which have been found to possess activity against various insects, and in particular show excellent residual activity against soil-dwelling insects such as Diabrotica.

Some types of trialkyl thiophosphonates are known in the art. U.S. Pat. No. 3,162,570, for instance, describes symmetrical trialkyl tri- and di-thiophosphonates including S,S-di-(n-butyl)-methyl- and -ethylphosphonotrithioates and -dithioates. This patent does not specifically disclose any compounds having an S,S-di(tertiary alkyl) structure.

U.S. Pat. No. 4,258,038 discloses a series of unsymmetrical trialkyl trithiophosphonates in which one alkyl group is a branched $C_3$-$C_8$ alkyl. Such compounds are disclosed as being superior to the symmetrical unbranched alkyls of U.S. Pat. No. 3,162,570, in having equal or better soil insecticidal activity and less phytotoxicity to corn.

It has now been found that certain tri- and di-thiophosphonates having an S,S-di-(tertiary alkyl) structure, show excellent control of insects, especially soil-borne insects, including rootworms and cutworms.

SUMMARY OF THE INVENTION

This invention relates to a series of thiophosphonate insecticides having the formula

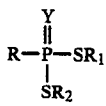

in which R is methyl or ethyl, Y is sulfur or oxygen and $R_1$ and $R_2$ are tertiary alkyl groups each having from 4 to 6 carbon atoms. $R_1$ and $R_2$ may be identical or different and include tertiary butyl, amyl, and hexyl groups. The term "tertiary amyl" refers to 1,1-dimethylpropyl group. When Y is sulfur, the compounds are trithiophosphonates; when Y is oxygen, they are dithiophosphonates.

This invention also relates to insecticidal compositions containing these novel compounds, methods of using both the compounds and the compositions for insect control, a process for producing one type of these compounds, namely, those which are symmetrical ($R_1$ and $R_2$ are identical tertiary alkyl groups), and a process for producing mercaptide salts which are useful as intermediates in the production of such symmetrical compounds, as well as for other purposes.

The term "insects" as used herein refers to the broad and commonly understood usage rather than to those creatures which in the strict biological sense are classified as insects, and includes, in addition to those belonging to the class Insecta, some classes of acarids such as spiders, mites, ticks, and the like, particularly mites.

Compounds in which $R_1$ and $R_2$ are identical, that is, symmetrical compounds, may be produced by reaction of the appropriate alkyl phosphonic or thiophosphonic dihalide (preferably dichloride) with two equivalents of an alkali metal mercaptide according to the reaction

in which Y, R and $R^1$ are as previously defined ($R_1 = R_2$); X stands for halogen, preferably chlorine, and M is an alkali metal, preferably sodium, potassium or lithium, most preferably sodium.

Reaction (1) is conducted in the presence of a solvent. Suitable solvents include aromatic hydrocarbons such as benzene or toluene, ethers such as diethyl ether, tetrahydrofuran, 1,4-dioxane and 1,2-dimethoxyethane, and mixtures of aromatic hydrocarbons with such ethers.

This reaction is generally conducted at temperatures of from about 0° C. to about 60° C., with a temperature of from about 50° to about 60° C. being preferred for trithioate products (Y is sulfur) and from about 0° to about 20° C. (most preferably from about 10° to about 15° C.) for dithioates (Y is oxygen).

The mercaptide salt may be prepared in any conventional way, such as by reaction of a tertiary alkyl mercaptan with an alkali metal hydroxide or alkoxide. Preferably, however, according to one aspect of this invention, the mercaptide is prepared by reaction of a tertiary alkyl mercaptan with an alkali metal or alkali metal hydride. Preferred reactants in this process are sodium and sodium hydride, respectively. These reactions can be represented as follows:

in which M and $R_1$ are as previously defined.

The mercaptide-producing reactions (2) and (3) are conducted in the presence of a solvent which is non-reactive under the reaction conditions, is preferably immiscible with water, and has a boiling point sufficiently high so that the total pressure during the reaction is approximately atmospheric but sufficiently low to permit its being stripped off from the ultimate thiophosphonate product at a reasonably low temperature (approximately 60° C.). Suitable solvents include those mentioned above for the production of the thiophosphonate product according to reaction (1). Preferred solvents are toluene and a mixture (50:50) of toluene and 1,4-dioxane.

When the alkali metal is used as the reactant (reaction (2)) the temperature should be above the melting point of the alkali metal. For instance, if sodium is used, the temperature should be above 98° C. If an alkali metal hydride is used (reaction (3)), the temperature may be lower, depending on the solvent and the particle size of the hydride, which is preferably used in the form of a powder. Maximum temperature in either case would be the boiling point of the solvent at the operating pressure. In any event, either the molten alkali metal or the alkali metal hydride powder is suspended in a solvent with rapid agitation and the tertiary alkyl mercaptan is slowly added. By-product hydrogen gas is vented to a condenser in which any unreacted mercaptan or entrained solvent is separated for return to the reactor. A slight excess of the alkali metal or alkali metal hydride is desirable but not essential. The reaction is considered complete when the evolution of hydrogen gas ceases.

In a preferred embodiment of the overall process, symmetrical S,S-di(tertiary alkyl) compounds are prepared by a one-reactor method combining reactions (2) or (3) with (1). First, the tertiary alkyl mercaptan is reacted with an alkali metal or alkali metal hydride to produce the alkali metal mercaptide. This reaction is conducted in the presence of a suitable solvent, which is then used for the second step, namely the production of the symmetrical thiophosphonate compound. This carried out by addition of the appropriate alkyl (thio)phosphonate dichloride according to reaction (1). After completion of the reaction, the product is isolated by appropriate steps, including washing, stripping, etc.

Compounds of the present invention in which $R_1$ and $R_2$ are not identical may be prepared by the following method.

In the first step, a tertiary alkyl mercaptan is reacted with an alkali metal or an alkali metal hydride, to produce a mercaptide salt, as in reaction (2) or (3).

In the second step, the mercaptide salt is reacted with the appropriate S-(tertiary alkyl), alkylphosphono(di)-thioic monohalide (preferably monochloride), according to the reaction

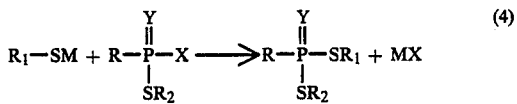

in which $R_1$, $R_2$, Y, M and X are as previously defined, but $R_1$ and $R_2$ are not identical.

The S-(tertiary alkyl) alkyl-phosphono(di)thioic halide may be prepared by any conventional means, such as by reaction of an alkyl mercaptan with an alkylphosphonothioic dihalide as described in U.S. Pat. No. 4,352,762 or with an alkyl phosphonic dihalide as described in U.S. Pat. No. 4,391,760.

Reaction (4) is generally carried out at a temperature of from about 0° C. to about 70° C., preferably from about 0° C. to about 25° C., in an organic solvent in the presence of a base. Suitable solvents include aromatic hydrocarbons such as benzene or toluene, and ethers such as diethyl ether, dimethoxyethane, or tetrahydrofuran. The desired product may be recovered by removal of the precipitated salt (MX), followed by evaporation of the solvent.

The following are examples of the preparation of compounds of this invention.

EXAMPLE 1

Preparation of S,S-(di-t-butyl) methylphosphonotrithioate (Compound 1 herein)

To a slurry of 63.0 grams (g) (2.62 mol) of oil-free sodium hydride in 2.75 liters of freshly distilled tetrahydrofuran, at 0° and under nitrogen, was added dropwise 214.1 g (270.0 ml, 2.38 mol) of 2-methyl-2-propanethiol. The mixture was then stirred for 15 minutes at 0° C., and to it was added dropwise 118.2 g (0.793 mol) of methylphosphonothioic dichloride. This mixture was stirred for 16 hours at room temperature, quenched with water, and extracted with ether. The ethereal solution was washed with saturated sodium chloride, dried with magnesium sulfate, and evaporated to an orange oil. The oil was dissolved in 1 liter of 98:2 hexane-acetone, treated with decolorizing charcoal, and filtered through a bed of 100 g of silica gel (fine mesh). Evaporation of the solvent yielded 151 g (74.4% of theoretical yield) of the title compound, a clear, nearly colorless oil. On standing, the oil crystallized—m.p. 35°–37° C. The structure was confirmed by nuclear magnetic resonance, infrared, and mass spectroscopy.

EXAMPLE 2

Preparation of S-t-Amyl S-t-butyl methylphosphonotrithioate (Compound 5 herein)

To a slurry of 0.49 g (0.0203 mole) of oil-free sodium hydride in 50 ml of freshly distilled tetrahydrofuran, at 0° C. and under nitrogen, was added dropwise a solution of 1.93 g (2.3 ml, 0.0185 mole) of 2-methyl-2-butanethiol in 15 ml of tetrahydrofuran. The mixture was then stirred for 45 minutes at room temperature and cooled to below 0° C. with an ice-salt bath. To it was added dropwise a solution of 3.0 g (0.0148 mole) of S-t-butyl methylphosphonodithioic chloride in 15 ml of tetrahydrofuran. After stirring at below 0° C. for 30 minutes, the mixture was filtered and 125 ml of ether was added to the filtrate. The ethereal solution was washed successively with water (2×50 ml) and brine (50 ml), dried with magnesium sulfate, and evaporated to a light yellow oil. The oil was dissolved in hexane-acetone (98/2), treated with decolorizing charcoal, and filtered through a bed of silica gel. Evaporation of the solvent afforded 3.3 g (82.5% of theoretical yield) of the title compound, a clear, colorless, mobile oil. The structure was confirmed by nuclear magnetic resonance, infrared and mass spectroscopy.

EXAMPLE 3

Preparation of S,S-(Di-t-amyl) methylphosphonodithioate)

(Compound 6 herein)

To a slurry of 1.79 g (0.0746 mole) of oil-free sodium hydride in 75 ml of freshly distilled tetrahydrofuran, at 0° C. and under nitrogen, was added dropwise a solution of 7.05 g (8.4 ml, 0.0678 mole) 2-methyl-2-butanethiol in 25 ml of tetrahydrofuran. The mixture was stirred for 1 hour at room temperature and then cooled to 0° C. To it was then added dropwise a solution of 3.0 g (0.0226 mole) of methylphosphonic dichloride in 25 ml of tetrahydrofuran. This mixture was then stirred at room temperature for 3 hours. The work-up procedure was performed as in Example 1 to provide 4.3 g (71%) of the title compound, a clear, colorless oil. The structure was confirmed by nuclear magnetic resonance, infrared, and mass spectroscopy.

EXAMPLE 4

Preparation of S,S-(Di-t-butyl) methylphosphonotrithioate (Compound 1 herein)

A 200-gallon reactor was filled with inert nitrogen gas and then charged with 447 pounds (lbs) (61 gallons) of toluene plus 534 lbs (62 gal) of 1,4-dioxane. While the mixed solvent was at ambient temperature, 26.2 lbs (1.14 lb-mol) of solid, metallic sodium was added without agitation. The reactor contents were heated to 101° C., the sodium was allowed to melt, and the agitator was started. A total of 95 lbs (14 gal, 1.04 lb-mol) of 2-methyl-2-propanethiol was gradually added to the reactor while maintaining the temperature at 99° C. The resulting hydrogen gas was passed through a condenser which condensed unreacted 2-methyl-2-propanethiol and returned it to the reactor. After the addition was completed, the reactor contents were allowed to react for 30 minutes, then the contents were cooled to 49° C. A total of 53 lbs (4 gal, 0.356 lb-mol) of methylphosphonothioic dichloride was gradually added to the agitated reactor while cooling to maintain the contents below 60° C. After the addition was completed, the reactor contents were heated to 60° C., were allowed to react for 1 hour, and then were cooled to 30° C. The organic mixture was washed sequentially with 37 gal of 2 wt.% NaOH solution, with 17 gal of 5 wt.% HCl solution, with 17 gal of 5 wt.% $NaHCO_3$ solution, and with 17 gal of pure water. The procedure for each wash consisted of adding the wash solution, agitating the reactor contents, allowing the contents to separate into two phases without agitation, and draining the wash solution from the reactor. After all four wash steps were completed, the reactor contents were heated to 50° C., and the mixed solvent was evaporated under vacuum until no more condensate would form in the condenser. Finally, a flow of nitrogen gas was bubbled through the remaining liquid at 50° C. until the last traces of mixed solvent were removed. The remaining liquid was drained from the reactor and allowed to crystallize. A total of 88.2 lbs of product was recovered; it contained 97.8 wt.% of the subject compound (theoretical yield=96.5%). The structure of the product was confirmed by gas chromatograph/mass spectrometer.

The following Table I depicts representative compounds of this invention, which may be prepared as previously described. Structures of these compounds were confirmed by analysis as above.

TABLE I $$R-\underset{\underset{SR_2}{|}}{\overset{\overset{Y}{\|}}{P}}-SR_1$$

| Compound Number | R | $R_1$ | $R_2$ | Y | m.p. °C., or $n_D^{30}$ |
|---|---|---|---|---|---|
| 1 | $CH_3$ | $t-C_4H_9$ | $t-C_4H_9$ | S | 35-37° C. |
| 2 | $C_2H_5$ | $t-C_4H_9$ | $t-C_4H_9$ | S | 1.5610 |
| 3 | $CH_3$ | $t-C_5H_{11}$ | $t-C_5H_{11}$ | S | 1.5622 |
| 4 | $CH_3$ | $t-C_4H_9$ | $t-C_4H_9$ | O | 55-57° C. |
| 5 | $CH_3$ | $t-C_4H_9$ | $t-C_5H_{11}$ | S | 1.5630 |
| 6 | $CH_3$ | $t-C_5H_{11}$ | $t-C_5H_{11}$ | O | 1.5187 |
| 7 | $C_2H_5$ | $t-C_4H_9$ | $t-C_4H_9$ | O | 1.5136 |

Insecticidal Evaluation Tests

The compounds in Table I above were tested for insecticidal activity using the following testing procedures. LD-50 values, based on the results of these tests, and/or calculated according to dosage-mortality curves, are expressed in Table II.

Housefly [*Musca domestica*]:

(a.) Contact: Test compounds were diluted in acetone and aliquots pipetted onto the bottom of aluminum dishes. To insure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 µg/25 female houseflies downward. The LD-50 values are expressed below in Table II under the heading "HF-C", in terms of µg of the test compound per 25 female flies.

(b.) Fumigant: Test compounds were diluted in acetone and aliquots pipetted onto 55 millimeter (mm) filter paper discs in the bottom of aluminum dishes. Immediately after the acetone had completely evaporated the dishes were placed in circular cardboard cages (volume—285 ml) containing 25 female houseflies. The cages were sealed on both ends with cellophane and each contained a sugar-water saturated cotton plug for maintenance of the flies. A piece of netting was placed over the aluminum dish in the cage in such a way that the flies were unable to come into direct contact with the chemically treated filter paper. Mortality was recorded after 48 hours. Test levels ranged from 100 µg/25 female houseflies downward. The LD-50 values are expressed in the following Table II under the heading "HF-F", in terms of µg of the test compound per 25 female houseflies per 285 ml volume of the test container.

Black Bean Aphid [*Aphis fabae* (Scop.)]:

Nasturtium plants (Tropaeolum sp.) approximately 5 cm tall, were transplanted into sandy loam soil in small cups and infested with 25-50 black bean aphids of mixed ages. Twenty-four hours later they were sprayed to the point of runoff with 50-50 acetone-water solutions of the test compounds. Treated plants were held in the greenhouse and mortality was recorded after 48 hours. Test concentrations ranged from 0.50% downward. The LD-50 values are expressed below in Table II under the heading "BA-C" in terms of percent of the test compound in the sprayed solution.

Tobacco Budworm [*Heliothis virescens* (Fabricius)]:

(a) Contact: Test compounds were diluted in a 50-50 acetone-water solution. Hyzini squash (*Calabacita abobrinha*) octyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LD-50 values are expressed below in Table II under the heading "TBW-C" in terms of percent of the test compound in the solution.

(b). Eggs: Paper towel patches of 2-day old eggs of the tobacco budworm were dipped in acetone solutions of the test compounds and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 values are expressed below in Table II under the heading "TBW-E" in terms of percent of the test compound in the solution.

Beet Armyworm [*Spodoptera exigua*]:

Test compounds were diluted in a 50-50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% or 0.025% downward. The LD-50 values are expressed below in Table II under the heading "BAW" in terms of percent of the test compound in solution.

Cabbage Looper [*Trichoplusia ni* (Hübner)]:

Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 values are expressed below in Table II under the heading "CL" in terms of percent of the test compound in this solution.

Western Spotted Cucumber Beetle Larvae [*Diabrotica undecimpunctata undecimpunctata* (Mannherheim)]:

Ten grams of moist potting soil was placed in a plastic cup. Test compounds were dissolved in acetone or an other appropriate solvent. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. Test concentrations ranged from 25 ppm downward. The LD-50 values are expressed below in Table II under the heading "Diabrotica" in terms of ppm of the test compound in the soil.

Black cutworm [(*Agrotis ipsilon*)]:

Soil Assay: Test compounds were dissolved in acetone and 0.05 ml aliquots were pipetted into small cups containing 10 grams of a soil mix. The compound was then incorporated into the soil with a mixer. A piece of lettuce was placed in each cup and five 3rd instar black cutworm larvae were introduced. The cups were capped and held for two days at constant temperature, then examined for live larvae. Test concentrations ranged from 25 ppm downwards. The LD-50 values are expressed below in Table II under the heading "BC-Soil" in terms of ppm of the test compound in the soil.

Foliar Assay: Test compounds were diluted in a 50-50 acetone-water solution. Cotyledons of hyzini squash (*Calabacita abobrinha*), approximately 1×¼ inches, were immersed in the test solutions for 2-3 seconds and placed on a wire screen to dry. The dried leaves were placed in petri dishes containing a moistened piece of filter paper and infested with 5 second-instar black cutworm larvae. The dishes were placed in a high humidity chamber. Mortality of the larvae was recorded 5 days later. Test concentrations ranged from 0.1% downward. The LD-50 values are expressed below in Table II under the heading "BC-Foliar" in terms of percent of the test compound in this solution.

Acaricidal Evaluation Test

The two-spotted mite (2SM) [*Tetranychus urticae* (Koch)] was employed in tests for miticides. The test procedure was as follows:

Pinto bean plants (Phaseolus sp.) approximately 10 cm tall, were transplanted into sandy loam soil in small cups and thoroughly infested with two-spotted mites of mixed ages and sexes. Twenty-four hours later the infested plants were inverted and dipped for 2-3 seconds in 50-50 acetone-water solutions of the test compounds. Treated plants were held in the greenhouse, and 7 days later mortality was determined for both adult mites and the nymphs hatching from eggs which were on the plants at the time of treatment. Test concentrations ranged from 0.05% downward. The LD-50 values are expressed below in Table II under the headings "2SM-A" (i.e., adults) and "2SM-E" (i.e. eggs) in terms of percent concentration of the test compound in the solution.

Systemic Evaluation Test

This test evaluates the root absorption and upward translocation of the candidate systemic compound. The two-spotted site (2SM) [*Tetranychus urticae* (Koch)] and the bean aphid (BA) [*Aphis fabae* (Scop.)] were employed in the test for systemic activity. Tests were conducted as follows;

Two-Spotted Mite

Test compounds were dissolved in acetone and aliquots diluted in 200 ml of water in glass bottles. Two pinto bean plants (Phaseolus sp.), with expanded primary leaves, were supported in each bottle by cotton plugs so that their roots and stems were immersed in the treated water. The plants were then infested with 75-100 two-spotted mites of various ages and sexes. One week later the mortality of the adult mites and nymphs was recorded. Test concentrations of the chemicals in the water ranged from 10 ppm downward. The LD-50 values are expressed in Table II under the heading "2-SM(S)" in terms of ppm of the test compound in the solution.

Black Bean Aphid [*Aphis fabae* (Scop.)]

Masturtium plants (Tropaeolum sp.), approximately 5 cm tall, were transplanted into 400 grams of sandy loam soil in one pint containers. Test chemicals were dissolved in acetone and aliquots diluted in 50-60 ml of water. The treated water was poured onto the surface of the soil and allowed to thoroughly soak in. The treated plants were infested with 25-50 black bean aphids of mixed ages and held in the greenhouse. Mortality was recorded after three days. Test concentrations ranged from 10 ppm down to that at which 50% mortality occurs. The LD-50 values are expressed in Table II under the heading "BA(S)" in terms of ppm of the test compound in the soil.

Soil Bioassay on Root Knot Nematode (*Meloidogyne incognita*)

A nematode colony was maintained on tomato plant roots (Lycopersicon sp.) grown in clay pots. Aliquots of nematode-infested soil were removed from these pots and placed in small cups. Test compounds were then incorporated into the soil. Four squash seeds were planted in each cup and washed as required.

Twenty-one days later the squash plants were removed and washed and the roots examined for the presence or absence of root nodules. Test concentrations ranged from 25 ppm (final concentration in the soil)

downward. The LD50 values are expressed in Table II under the heading "RKN" in terms of ppm of the test compound in the soil.

TABLE II

(LD$_{50}$)

| Cmpd. No. | HF, μg C | HF, μg F* | RA C, % | RA S, ppm | 2-SM A, % | 2-SM S, ppm | 2-SM E, % | TBW, % C | TBW, % E | BAW, % | CL, % | BC, soil, ppm | BC, foliar, % | RKN, ppm | Diabrotica, ppm (soil) |
|---|---|---|---|---|---|---|---|---|---|---|---|---|---|---|---|
| 1 | 47 | 19 | 0.002 | 0.5 | 0.005 | >10 | 0.008 | 0.004 | 0.002 | 0.018 | 0.0025 | 2.1 | 0.003 | 4 | 0.063 |
| 2 | 35 | 12 | 0.003 | 3 | 0.004 | >10 | 0.004 | 0.0025 | 0.002 | 0.017 | 0.006 | 4.1 | 0.01 | 7.5 | 0.09 |
| 3 | 15 | 17 | 0.002 | 6 | 0.05 | >10 | 0.05 | 0.02 | 0.005 | 0.006 | 0.0008 | >10 | 0.012 | 7.5 | 0.4 |
| 4 | 30 | 15 | 0.001 | 0.6 | >0.05 | >10 | >0.05 | 0.0025 | 0.0035 | 0.016 | 0.002 | 5.8 | 0.004 | 4 | 0.08 |
| 5 | 30 | 15 | 0.0006 | 6 | 0.05 | >10 | >0.05 | 0.004 | 0.002 | >0.025 | 0.003 | 4.2 | 0.005 | 10 | 0.2 |
| 6 | 10 | 50 | 0.001 | 3 | >0.05 | >10 | >0.05 | 0.003 | 0.003 | >0.025 | 0.005 | >10 | 0.004 | 4 | 0.4 |
| 7 | 35 | 28 | 0.003 | 4 | 0.006 | >10 | 0.006 | 0.005 | 0.002 | 0.007 | 0.002 | 6.25 | — | 4 | 0.09 |

Key:
C = Contact Test
F = Fumigate Test
S = Systemic Test
E = Test on Eggs
A = Test on adults
* = Per 285 ml volume container

Residual Soil Bioassay on Diabrotica

Test compounds were diluted in acetone and pipetted into containers holding 900 grams of dry sandy loam soil. The compounds were incorporated into the soil by vigorous shaking. Then, 100 ml of deionized water was added; the containers were covered and stored at 78° F. (25.5° C.).

Soil samples of 10 g of each were removed from the containers at weekly intervals and placed in small cups, together with approximately 50 eggs of *Diabrotica undecimpunctata undecimpunctata* (Mannerheim). A piece of Romaine lettuce was added 3-4 days later. The lettuce was examined 7-9 days after addition of lettuce for larval feeding.

Test compounds were variously incorporated into soil at concentrations in the soil of 1 and 2 ppm. Table III indicates the number of weeks of Diabrotica control (100% mortality) exhibited by the test compounds.

TABLE III

Residual Control of Diabrotica

| Compound No. | Weeks Control (100% Mortality) 1 ppm | Weeks Control (100% Mortality) 2 ppm |
|---|---|---|
| 1 | 31 | >45 |
| 2 | >41 | >41 |
| 3 | — | 10 |
| 4 | 22 | >40 |
| 5 | 19 | 30 |
| 6 | — | 17 |
| 7 | — | — |

In practice, a pure compound can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives, thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be microcapsules or encapsulated form, to permit release of the enclosed active compound at a controlled rate over a period of time. Liquid compositions of this type contain encapsulated droplets of approximately 1-50 microns in diameter, including the active compound and optionally a solvent. The encapsulating material is an inert porous membrane of a polymeric material.

Solid encapsulated compositions generally take the form of granules, in which the liquid containing the active compound is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | Weight % |
| --- | --- |
| Composition A: Granular Solid | |
| Active Compound | 10 |
| diatomaceous earth granules | 85 |
| triethylene glycol | 5 |
| Total | 100% |
| Composition B: Wettable Powder | |
| Active Compound | 80 |
| wetting agent (sodium dialkyl-naphthalene sulfonate) | 1 |
| dispersing agent (sodium lignosulfonate) | 4 |
| diluent (aluminum magnesium | 15 |

-continued

| Component | Weight % |
|---|---|
| silicate | |
| Total | 100% |
| Composition C: Dilute Solution | |
| Active Compound | 5 |
| solvent (xylene) | 95 |
| Total | 100% |
| Composition D: Emulsifiable Concentrate | |
| Active Compound | 50 |
| Emulsifier (blend of metal sulfonates and polyoxyethylene ethers) | 10 |
| solvent (xylene) | 40 |
| Total | 100% |
| Composition E: Concentrated Solution | |
| Active Compound | 90 |
| solvent (xylene) | 10 |
| Total | 100% |
| Composition F: Granular Solid | |
| Active Compound | 5 |
| diatomaceous earth granules | 90 |
| dipropylene glycol | 5 |
| Total | 100% |

What is claimed is:

1. A compound having the formula

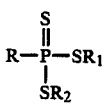

in which R is methyl or ethyl, and $R_1$ and $R_2$ are tertiary alkyl groups each having from 4 to 6 carbon atoms.

2. A method of controlling insects comprising applying to said insect or to a locus at which control is desired an insecticidally effective amount of a compound according to claim 1.

3. A method of controlling insects according to claim 2 in which the compound is applied to soil to control insects which may be present therein.

4. A compound having the formula

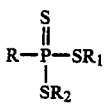

in which R is methyl or ethyl, and $R_1$ and $R_2$ are identical tertiary alkyl groups each having from 4 to 6 carbon atoms.

5. A compound having the formula

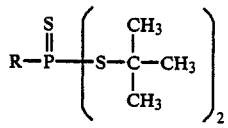

in which R is methyl or ethyl.

6. A compound having the formula

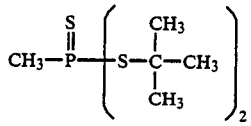

7. A compound having the formula

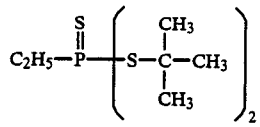

8. A compound having the formula

in which R is methyl or ethyl and $R_1$ and $R_2$ are tertiary alkyl groups each having from 5 to 6 carbon atoms.

9. A method of controlling insects comprising applying to said insect or to a locus at which control is desired an insecticidally effective amount of a compound according to claim 4.

10. A method of controlling insects according to claim 9 in which the compound is applied to soil to control insects which may be present therein.

11. A method of controlling insects comprising applying to said insect or to a locus at which control is desired as insecticidally effective amount of a compound according to claim 5.

12. A method of controlling insects according to claim 11 in which the compound is applied to soil to control insects which may be present therein.

13. A method of controlling insects comprising applying to said insect or to a locus at which control is desired an insecticidally effective amount of a compound according to claim 6.

14. A method of controlling insects according to claim 13 in which the compound is applied to soil to control insects which may be present therein.

15. A method of controlling insects comprising applying to said insect or to a locus at which control is desired an insecticidally effective amount of a compound according to claim 7.

16. A method of controlling insects according to claim 15 in which the compound is applied to soil to control insects which may be present therein.

17. A method of controlling insects comprising applying to such insect to or a locus at which control is desired an insecticidally effective amount of a compound according to claim 8.

18. A method of controlling insects according to claim 17 in which the compound is applied to soil to control insects which may be present therein.

19. A method for controlling root knot nematodes comprising applying to said nematode or to a locus at which control is desired a nematocidally effective amount of a compound according to claim 1.

20. A method for controlling root knot nematodes comprising applying to said nematode or to a locus at which control is desired a nematocidally effective amount of a compound according to claim 5.

21. A method for controlling root knot nematodes comprising applying to said nematode or to a locus at which control is desired a nematocidally effective amount of a compound according to claim 6.

22. A method for controlling root knot nematodes comprising applying to said nematode or to a locus at which control is desired a nematocidally effective amount of a compound according to claim 7.

23. An insecticidal or nematocidal composition of matter comprising:
    (a) an insecticidally or nematocidally effective amount of a compound according to claim 1; and
    (b) an insecticidally or nematocidally suitable diluent or carrier.

24. An insecticidal or nematocidal composition of matter comprising:
    (a) an insecticidally or nematocidally effective amount of a compound according to claim 9; and
    (b) an insecticidally or nematocidally suitable diluent or carrier.

25. An insecticidal or nematocidal composition of matter comprising:
    (a) an insecticidally or nematocidally effective amount of a compound according to claim 5; and
    (b) an insecticidally or nematocidally suitable diluent or carrier.

26. An insecticidal or nematocidal composition of matter comprising:
    (a) an insecticidally or nematocidally effective amount of a compound according to claim 6; and
    (b) an insecticidally or nematocidally suitable diluent or carrier.

27. An insecticidal or nematocidal composition of matter comprising:
    (a) an insecticidally or nematocidally effective amount of a compound according to claim 7; and
    (b) an insecticidally or nematocidally suitable diluent or carrier.

28. An insecticidal or nematocidal composition of matter comprising:
    (a) an insecticidally or nematocidally effective amount of a compound according to claim 8; and
    (b) an insecticidally or nematocidally suitable diluent or carrier.

* * * * *

UNITED STATES PATENT AND TRADEMARK OFFICE
CERTIFICATE OF CORRECTION

PATENT NO.   :   4,752,604
DATED        :   June 21, 1988
INVENTOR(S)  :   Charles G. Chavdarian et al.

It is certified that error appears in the above-identified patent and that said Letters Patent is hereby corrected as shown below:

Please delete the name of Jonathan P. Earhart as an inventor.

In column 3, at line 11, please add the word "is" between the words "This" and "carried".

In Claim 11, third line, please delete the word "as" and insert therefor the word -- an --.

In Claim 24, fourth line, please change the phrase "Claim 9" to read --- Claim 4 ---.

Signed and Sealed this

Third Day of January, 1989

*Attest:*

DONALD J. QUIGG

*Attesting Officer*   *Commissioner of Patents and Trademarks*